United States Patent [19]

Besins

[11] 4,196,188
[45] Apr. 1, 1980

[54] ORALLY ADMINISTRABLE FORM OF PROGESTERONE

[76] Inventor: Jean-Louis A. Besins, 23 rue Raynouard, 75016 Paris, France

[21] Appl. No.: 759,277

[22] Filed: Jan. 12, 1977

[51] Int. Cl.$^2$ .............................................. A61K 9/48
[52] U.S. Cl. ...................................... 424/37; 424/242; 424/243
[58] Field of Search ........................ 424/37, 238, 243

[56] References Cited
U.S. PATENT DOCUMENTS

| 3,284,303 | 11/1966 | Meli | 424/242 |
| 3,342,682 | 9/1967 | Brcoli | 424/238 |
| 3,828,106 | 8/1974 | Rudez | 424/242 X |
| 3,862,311 | 1/1975 | Leeson | 424/242 X |

Primary Examiner—Shep K. Rose
Attorney, Agent, or Firm—Gifford, Chandler, VanOphem, Sheridan & Sprinkle

[57] ABSTRACT

The present invention relates to an orally active pharmaceutical preparation comprised of progesterone, finely ground such that 80% of the progesterone particles are about 1–15 microns in size, suspended in an excipient and contained in capsules. The drug effects increased progestational and contraceptive activity at this particle size.

1 Claim, No Drawings

ORALLY ADMINISTRABLE FORM OF PROGESTERONE

BACKGROUND OF THE INVENTION

1. Field of the Invention

Progesterone is a well-known natural hormone which is, in practice, only administered by injection, and otherwise in the form of delayed release derivatives, in cases of hormone deficiency of the corpus luteum, especially in cases of infertility.

2. Description of the Prior Art

The administration of progesterone by the oral route has been abandoned because of its destruction in the digestive tract which occurs more rapidly than its absorption, to a point such that even daily doses of one or two grams are still insufficient to give rise to a net progestational action.

As a result, up to the present day, the only method for obtaining progestational action by oral administration has consisted in using synthetic derivatives such as medroxyprogesterone, norethisterone, methylestrenolone, chlormadinone acetate, 6-dehydroretroprogesterone or lynestrenol.

However, these derivatives suffer from a number of disadvantages. In the first case, their activities are not wholly identical with those of progesterone. Thus, certain of the derivatives possess a notable androgenic activity, giving rise to a long term risk of virilisation, as well as a risk of masculinisation of the foetus in the case of treatment in the course of pregnancy. Others of the derivatives possess a long term estrogenic activity.

Further, in contradistinction to progesterone, certain of the derivatives do not possess anti-estrogenic activity, anti-aldosteronic activity or anti-ovulatory activity.

Secondly, these derivatives give rise to problems of tolerance, which manifest themselves as digestive troubles, the onset of migraine or headaches and even the risk of veinous thrombosis. Accordingly, the Applicant has carried out research with a view to providing a form of progesterone which is effectively administrable by the oral route, whilst giving rise to all its properties, and without secondary effects, as well as a practical method for preparing this form of progesterone and presenting it to the patient, on a commercial scale.

SUMMARY OF THE INVENTION

In accordance with the invention the therapeutically effective form for oral administration of progesterone consists of particles micronised to a particle size of less than 15 microns.

The invention also provides, as indicated above, a composition for the therapeutically effective administration of progesterone, for its usual applications, characterized in that it contains, as active constituent, micronised progesterone of which at least 80% of the particles have a particle size between 1 and 15 microns, together with an appropriate vehicle or excipient which, as will be discussed below, is preferably an oil or an oily product.

DESCRIPTION OF THE PRESENT INVENTION

Thus it has been found that if progesterone is micronised to such a particle size, and administered by the oral route, it is assimilated at at rate greater than the rate of its destruction in the digestive tract, thereby exercising its progestational activity whilst being free from all unwanted secondary side effects.

More particularly, the applicant has carried out experiments to determine the critical character of the particle size in both animal and human trials.

The particle size analysis of the progesterone under trial was carried out using a Coulter Counter, Model TA 2, which is an automatic apparatus for analysing particle size distribution of powders. This apparatus makes it possible to detect particles independently of their form, their density or their colour, and the measure of the size is a direct function of their volume and thus of their mass. The apparatus operates over such a scale that it is possible to differentiate between particles whose mass varies from 0.04 microns to several hundreds of microns. The analysis is carried out on several hundred thousands of particles as a result of which it is possible to carry out a valid check on the particle size distribution.

These various advantages give the results of the analysis obtained by this method an exactitude, a precision and a reproducibility which cannot be obtained by other conventional methods for granulometric analysis.

Experience shows that for the application envisaged, the progesterone particles should have a particle size of less than 15 microns.

The test used to establish this limit consists in measuring the level of progesterone in plasma by the radioimmunological method using double isotopic labelling and chromatography (Scholler-Mauvais-Jarvis).

Animal Trials

In the course of pharmacological trials on animals, there were measured the progesterone plasma levels after administration of different doses of progesterone having different particle sizes by the oral route to castrated rats. The two dosage rates used were 5 mg/kg and 10 mg/kg.

The two types of progesterone had particle sizes of 5 microns and of 100 microns. Administration was effected by forced feeding of fasting animals with the progesterone suspended in carboxymethyl cellulose. Blood samples were taken two hours and four hours after administration of the progesterone. The plasma progesterone levels were measured by the radioimmunological method using an antiserum from the Institut Pasteur. The results obtained are given in Table 1 below.

TABLE 1

|  |  | 2h | 4h |
|---|---|---|---|
| 5 mg/Kg | 100μ | 22.5 ± 1 | 15 ± 2.5 |
|  | 5 μ | 31 ± 6.5 | 34 ± 7.5 |
| 10 mg/Kg | 100μ | 28.5 ± 3.5 | 10 ± 5 |
|  | 5 μ | 32.5 ± 5 | 24 ± 4 |

The following comments may be made in view of these results.

1. The plasma concentrations measured are not (at the doses used) a function of the dose administered; the results are practically identical with the two doses used of 5 mg/Kg and 10 mg/KG.

2. At a dose at 5 mg/Kg the plasma concentrations are higher when the progesterone is micronised to 5 microns than when it is micronised to 100 microns. At this dosage and at the time of four hours the difference is significant.

3. At the two dosages employed, 5 mg/Kg and 10 mg/Kg, the plasma concentrations are comparable after two hours and four hours for the progesterone micronised to 5 microns. On the contrary, for the progesterone micronised to 100 microns, the plasma concentrations are significantly less four hours after administration than two hours after administration.

II—Human Trials

In man, progesterone micronised in accordance with the invention is administered by the oral route in the form, for example, of gelules or soft gelatine capsules at doses of from 100 to 200 mg to exercise its progestational and contraceptive activity.

The results of these trials, namely the plasma levels with different doses of micronised progesterone, the pharmaceutical presentation being as described above, are given in Table 2 below.

TABLE 2

|  |  | 2h | 6h | 24h |
|---|---|---|---|---|
| 100μ | 200 mg | 16 | 7 | 0.6 |
| 20μ | 200 mg | 27 | 7.4 | 3.5 |
|  | 100 mg | 14 | 8 | 4 |
| 10μ | 200 mg | 78 | 17 | 2.5 |
| 5μ | 200 mg | 62 | 7 | 1.6 |
| After 3 months storage |  | 17 | 3.5 | 3 |
| 10μμ | 200 mg | 25.3 | 9.2 | 6.8 |
|  | 100 mg | 8.8 | 5.4 | 8.6 |

It will be clearly seen from Table 2 that the same observations as given for the results summarised in Table 1, apply.

It is convenient to note that the method of preparation of the micronised progesterone compositions in accordance with the invention is of importance.

In the first case, the technique employed for micronisation of the progesterone implies a certain number of important conditions; thus in order to obtain a given, constant granulometry for each operation, it is necessary to start from a particular crystalline form of progesterone, obtained by recrystallization, whatever may be the physical characteristics of the starting progesterone.

To this end, in a first stage, the progesterone is dissolved, at 60° C. in acetone at a ratio of one part of progesterone to two volumes of acetone. The solution is then filtered and the progesterone is recrystallized by progressive cooling with stirring.

The evolution of temperatures during the course of the cooling must be rigourously followed in order to obtain a regular constant crystal form. The final temperature is 5° C. The yield of this crystallization is about 90%. The crystals obtained are dried under vacuum until all the acetone has been removed. In the second step, the micronisation proper should be carried out in a high speed rotor mill containing one part of arachid oil (codex) for one part of progesterone. The time of milling or grinding will be a function of the capacity and type of apparatus used. This must be calibrated with increasing grinding times to obtain a given granulometry. The length of grinding may vary from half an hour to three hours.

The grinder or mill must be provided with a cooling system to maintain the temperature between 25° and 30° C. All parts of the grinder in contact with the progesterone should be made of stainless steel. It is preferable to carry out grinding under nitrogen.

The progesterone thus micronised must then be formulated in the appropriate pharmaceutical form. In this regard, it is convenient to note that compressed forms such as dragees, tablets, pilules, etc. may not be used since all these dry oral dosage unit forms necessitate at one stage or another in their preparation a more or less great compression of the ingredients. It is known that compression modifies the granulometric distribution of the starting particles. Thus, if one starts with an initial powder having a fixed particle size, disintergration after compression, even light compression, of the particles gives rise to very different particle sizes and hence gives rise to a very different bioavailability.

Accordingly, the micronised progesterone in accordance with the invention should be presented in the form of gelules which overcome the above disadvantages since one may thus reduce or even eliminate all compression of the product during the course of filling of the gelule. However, when micronised to a particle size of less than twenty microns, the product becomes very hygroscopic and electrostatic and is thus very difficult to handle. Further, in the course of time, a modification of the granulometric distribution is noted in that the average particle size increases, leading to a significant reduction in the plasma levels after absorption, as shown in Table 3 below.

TABLE 3

| Particle size | DOSE | 2h | 6h |
|---|---|---|---|
| 5μ fresh product | 200 mg | 62 | 7 |
| after 3 months storage |  | 17 | 3.5 |

All these problems can be overcome, however, if the quantity of micronised progesterone to be administered only represents a small percentage of the total weight of the gelule. However, with regard to the dose of the order of from 100 to 200 mg necessary to obtain plasma levels corresponding to the desired therapeutic activity, the major part of the contents of the gelule must comprise the active principal.

Accordingly, the applicants have been led to another pharmaceutical form which permits the administration, by the oral route, of a liquid or semi-liquid or pasty product, in the absence of water—namely the soft capsule.

In view of the method of production of such soft capsules, the excipient is an oil or other analogous oily product, which permits filling of the capsule by flowing the composition into the capsule. It is for this reason that the process in accordance with the invention, consisting of micronising the progesterone directly in the oily phase, is carried out since this makes it possible to immediately fill the desired product into capsules without the risk of modifying the granulometric distribution of the micronised material in the course of various handling operations and also facilitates storing of the product. Further, micronisation itself is carried out more easily in the oily phase than in the dry or aqueous phase and thus overheating, always undesirable, of the active principle is avoided and the necessity for cooling and lubricating the course of the micronisation is also avoided.

It is convenient to note that the German chemical firm Schering have suggested, among their products, a micronised progesterone but as chemical product, sold as such, without any definite pharmaceutical form, without specifying any particular use and, particularly, without indicating any particular properties or applications. Accordingly, this is the first time progesterone has been presented as such as a medicament which may be effectively administered by the oral route in a form capable of exercising all the effects of endogenous progesterone, without secondary effects. On the one hand there is the anticonceptional effect of progestational agents and on the other hand a true substitutive activity in all cases of luteal insufficiency.

The indications for the compositions of the invention are, therefore, the following:

Luteal insufficiency as evidenced by premenstrual anxiety
dysmenorrheia
functional meno-metrorragia foctionelle
amenorrheia benign mastodynia of mastophathia
Seborrhea, acne, seborrhic alopeacidia
Endometriosis
Threatened Abortion
Contraception Having described my invention, many modifications thereto will become apparent to those skilled in the art to which it pertains without departing from the spirit of the invention as defined by the scope of the appended claims.

I claim:

1. An effective orally administrable soft gelatin capsule essentially containing micronised particles of recrystallized progesterone at least 80% having a particle size of from 5 to less than about 15 microns, in an oil vehicle, said micronized particles having been micronized in said oil phase.

* * * * *